(12) United States Patent
Lv et al.

(10) Patent No.: US 10,426,205 B2
(45) Date of Patent: Oct. 1, 2019

(54) INTELLIGENT FABRIC, INTELLIGENT SHOE AND INTELLIGENT GARMENT (71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Zhenhua Lv, Beijing (CN); Shijun Wang, Beijing (CN); Lei Wang, Beijing (CN); Xiaochuan Chen, Beijing (CN); Hailin Xue, Beijing (CN); Wenbo Jiang, Beijing (CN); Yue Li, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 320 days.

(21) Appl. No.: 15/130,000

(22) PCT Filed: Oct. 22, 2015

(86) PCT No.: PCT/CN2015/092493
§ 371 (c)(1),
(2) Date: Sep. 28, 2016

(87) PCT Pub. No.: WO2016/201846
PCT Pub. Date: Dec. 22, 2016

(65) Prior Publication Data
US 2017/0112201 A1  Apr. 27, 2017

(30) Foreign Application Priority Data
Jun. 18, 2015  (CN) .......................... 2015 1 0342187

(51) Int. Cl.
A41D 13/005 (2006.01)
A43B 1/00 (2006.01)
(Continued)

(52) U.S. Cl.
CPC .......... *A41D 13/005* (2013.01); *A41D 1/002* (2013.01); *A41D 27/285* (2013.01);
(Continued)

(58) Field of Classification Search
None
See application file for complete search history.

(56) References Cited

U.S. PATENT DOCUMENTS 9,332,792 B2 * 5/2016 Harber ................. A41D 13/002
2005/0249917 A1 * 11/2005 Trentacosta ....... B01D 39/1692
428/137
(Continued)

FOREIGN PATENT DOCUMENTS

| CN | 102963078 A | 3/2013 |
| CN | 203873046 U | 10/2014 |

(Continued)

OTHER PUBLICATIONS

Chinese First Office Action for Chinese Application No. 201510342187. 8, dated Dec. 16, 2015, 8 Pages.
(Continued)

*Primary Examiner* — Bickey Dhakal
(74) *Attorney, Agent, or Firm* — Brooks Kushman P.C.

(57) ABSTRACT

An intelligent fabric includes: a base layer provided with vent holes and a thermal insulation layer arranged on the base layer and moved relative to the base layer; a temperature sensor configured to detect temperature information; and a controller connected to the temperature sensor and the thermal insulation layer, and configured to control the thermal insulation layer to be moved relative to the base layer in
(Continued)

accordance with the temperature information detected by the temperature sensor, to switch the thermal insulation layer between a state where the thermal insulation layer covers the vent holes completely and a state where the thermal insulation layer does not cover the vent holes, or among the above two states and a state where the thermal insulation layer covers a portion of the vent holes.

20 Claims, 11 Drawing Sheets

(51) Int. Cl.
*A41D 1/00* (2018.01)
*A41D 27/28* (2006.01)
*A43B 3/00* (2006.01)
*A43B 5/00* (2006.01)
*A43B 7/08* (2006.01)
*A61B 5/01* (2006.01)
*B32B 3/26* (2006.01)
*B32B 5/02* (2006.01)
*A43B 7/00* (2006.01)
*A43B 7/02* (2006.01)
*A43B 23/02* (2006.01)
*A61B 5/00* (2006.01)
*B32B 5/04* (2006.01)
*A41D 31/06* (2019.01)
*A41D 13/002* (2006.01)

(52) U.S. Cl.
CPC .............. *A41D 31/065* (2019.02); *A43B 1/00* (2013.01); *A43B 3/0005* (2013.01); *A43B 5/00* (2013.01); *A43B 7/005* (2013.01); *A43B 7/02* (2013.01); *A43B 7/085* (2013.01); *A43B 7/087* (2013.01); *A43B 23/0205* (2013.01); *A43B 23/0235* (2013.01); *A61B 5/01* (2013.01); *A61B 5/6804* (2013.01); *B32B 3/266* (2013.01); *B32B 5/02* (2013.01); *B32B 5/04* (2013.01); *A41D 13/002* (2013.01); *A61B 5/6807* (2013.01); *A61B 2503/10* (2013.01); *A61B 2562/0271* (2013.01); *B32B 2307/304* (2013.01); *B32B 2307/51* (2013.01); *B32B 2307/546* (2013.01); *B32B 2437/02* (2013.01); *B32B 2457/00* (2013.01)

(56) References Cited

U.S. PATENT DOCUMENTS

| | | | |
|---|---|---|---|
| 2012/0114883 | A1 | 5/2012 | Kapur et al. |
| 2012/0292304 | A1* | 11/2012 | Burchard ............... G05D 23/19 |
| | | | 219/386 |
| 2015/0230563 | A1* | 8/2015 | Bacino ................... A43B 7/125 |
| | | | 36/43 |

FOREIGN PATENT DOCUMENTS

| | | |
|---|---|---|
| CN | 104216440 A | 12/2014 |
| CN | 204273317 U | 4/2015 |
| CN | 104872873 A | 9/2015 |
| CN | 204838144 U | 12/2015 |

OTHER PUBLICATIONS

International Search Report and Written Opinion for PCT Application No. PCT/CN2015/092493, dated Feb. 16, 2016, 13 Pages.

* cited by examiner

INTELLIGENT FABRIC, INTELLIGENT SHOE AND INTELLIGENT GARMENT

CROSS-REFERENCE TO RELATED APPLICATION

This application is the U.S. national phase of PCT Application No. PCT/CN2015/092493 filed on Oct. 22, 2015, which claims priority to Chinese Patent Application No. 201510342187.8 filed on Jun. 18, 2015, the disclosures of which are incorporated in their entirety by reference herein.

TECHNICAL FIELD

The present disclosure relates to the field of health care technology, in particular to an intelligent fabric, an intelligent shoe and an intelligent garment.

BACKGROUND

More and more people take exercises, e.g., running and playing ball games, so as to keep fit. Usually, at a low temperature, people will be dressed in thick sportswear, which causes that sweat generated by the people during the exercise will be prevented from being evaporated in time. In the case that people are dressed in thin sportswear, they will feel cold before the exercise or it is impossible to maintain their body temperatures after the exercise, so they will catch cold easily.

SUMMARY

An object of the present disclosure is to provide an intelligent fabric, an intelligent shoe and an intelligent garment, so as to keep a user warm in the case of a low body temperature and dissipate heat rapidly in the case of a high body temperature.

In one aspect, the present disclosure provides in some embodiments an intelligent fabric, including: a base layer provided with vent holes and a thermal insulation layer arranged on the base layer and capable of being moved relative to the base layer; a temperature sensor configured to detect temperature information; and a controller connected to the temperature sensor and the thermal insulation layer, and configured to control the thermal insulation layer to be moved relative to the base layer in accordance with the temperature information detected by the temperature sensor, so as to switch the thermal insulation layer between a state where the thermal insulation layer covers the vent holes completely and a state where the thermal insulation layer does not cover the vent holes, or among the state where the thermal insulation layer covers the vent holes completely, a state where the thermal insulation layer partially covers the vent holes, and the state where the thermal insulation layer does not cover the vent holes.

Optionally, in the case that the thermal insulation layer is switched between the state where the thermal insulation layer covers the vent holes completely and the state where the thermal insulation layer does not cover the vent holes, the controller includes: a first comparator connected to the temperature sensor and configured to compare the temperature information detected by the temperature sensor with a temperature threshold; and a first control unit connected to the first comparator and the thermal insulation layer, and configured to, in the case that the first comparator determines that the temperature information detected by the temperature sensor is less than or equal to the temperature threshold, control the thermal insulation layer to completely cover the vent holes, and in the case that the first comparator determines that the temperature information detected by the temperature sensor is greater than the temperature threshold, enable the thermal insulation layer not to cover the vent holes.

Optionally, in the case that the thermal insulation layer is switched among the state where the thermal insulation layer covers the vent holes completely, the state where the thermal insulation layer partially covers the vent holes and the state where the thermal insulation layer does not cover the vent holes, the controller includes: a second comparator connected to the temperature sensor, and configured to compare the temperature information detected by the temperature sensor with a first threshold and a second threshold greater than the first threshold; and a second control unit connected to the second comparator and the thermal insulation layer, and configured to, in the case that the second comparator determines that the temperature information detected by the temperature sensor is less than or equal to the first threshold, control the thermal insulation layer to completely cover the vent holes, in the case that the second comparator determines that the temperature information detected by the temperature sensor is between the first threshold and the second threshold, control the thermal insulation layer to partially cover the vent holes, and in the case that the second comparator determines that the temperature information detected by the temperature sensor is greater than or equal to the second threshold, control the thermal insulation layer not to cover the vent holes.

Optionally, the controller includes: a stationary rod fixed onto the base layer; a mobile rod movably arranged on the base layer and opposite to the stationary rod, and capable of being moved along the base layer close to, or away from, the stationary rod; and a driving member connected to the mobile rod, and configured to drive the mobile rod to be moved close to, or away from, the stationary rod in accordance with the temperature information detected by the temperature sensor. One end of the thermal insulation layer is connected to the mobile rod, and the other end of the thermal insulation layer is fixed onto one end of the base layer. In the case that the mobile rod is moved close to the stationary rod, more area of each vent hole is covered by the thermal insulation layer, and in the case that the mobile rod is moved away from the stationary rod, less area of each vent hole is covered by the thermal insulation layer.

Optionally, the controller includes: a stationary rod fixed onto the base layer; a mobile rod movably arranged on the base layer and opposite to the stationary rod, and capable of being moved along the base layer close to, or away from, the stationary rod; and a driving member connected to the mobile rod, and configured to drive the mobile rod to be moved close to, or away from, the stationary rod in accordance with the temperature information detected by the temperature sensor. One end of the thermal insulation layer is connected to the mobile rod, and the other end of the thermal insulation layer is fixed onto the stationary rod. In the case that the mobile rod is moved close to the stationary rod, less area of each vent hole is covered by the thermal insulation layer, and in the case that the mobile rod is moved away from the stationary rod, more area of each vent hole is covered by the thermal insulation layer.

Optionally, the driving member includes: an elastic, telescopic member configured to connect the stationary rod to the mobile rod; and a control member connected to the elastic, telescopic member, and configured to control a telescopic movement of the elastic, telescopic member in accordance with the temperature information detected by the temperature sensor, so as to drive the mobile rod to be moved close to, or away from, the stationary rod.

Optionally, the driving member further includes two opposite sliding rails, and two ends of the mobile rod are arranged in the two sliding rails respectively.

Optionally, the base layer includes a first end and a second end opposite to the first end. The controller includes: a mobile rod movably arranged on the base layer and capable of being moved along the base layer to close to, or away from, the second end of the base layer; and a driving member connected to the mobile rod and configured to drive the mobile rod to be moved close to, or away from, the second end of the base layer in accordance with the temperature information detected by the temperature sensor. One end of the thermal insulation layer is connected to the first end of the base layer, and the other end of the thermal insulation layer is connected to the mobile rod. In the case that the mobile rod is moved close to the second end of the base layer, more area of each vent hole is covered by the thermal insulation layer, and in the case that the mobile rod is moved away from the second end of the base layer, less area of each vent hole is covered by the thermal insulation layer.

Optionally, the driving member includes: an elastic, telescopic member configured to connect the mobile rod to the second end of the base layer; and a control member connected to the elastic, telescopic member, and configured to control a telescopic movement of the elastic, telescopic member in accordance with the temperature information detected by the temperature sensor, so as to drive the mobile rod to be moved close to, or away from, the second end of the base layer.

Optionally, the thermal insulation layer is made of a flexible, foldable fabric or an elastic, telescopic fabric.

Optionally, the base layer includes a stationary spindle, and a plurality of stationary sectors arranged fixedly around the stationary spindle. The stationary sectors are arranged at intervals, and a vent hole is arranged between each two adjacent stationary sectors. The thermal insulation layer includes a plurality of rotatable sectors arranged around the stationary spindle. The rotatable sectors are arranged at intervals, and each of the rotatable sectors has a shape adapted to a shape of the vent hole. The controller includes a driving member connected to the rotatable sectors and configured to drive the rotatable sectors to rotate around the stationary spindle in accordance with the temperature information detected by the temperature sensor, so as to enable the rotatable sectors to cover each of the vent holes partially, cover the vent holes completely, or not to cover the vent holes.

In another aspect, the present disclosure provides in some embodiments intelligent shoe including a sole and an upper portion arranged on the sole and at least partially made of the above-mentioned intelligent fabric.

Optionally, each intelligent shoe is made by joining a common fabric and the intelligent fabric.

Optionally, the intelligent fabric is arranged at a position corresponding to an upper surface, a side surface or an ankle portion of the upper portion.

In yet another aspect, the present disclosure provides in some embodiments an intelligent garment at least partially made of the above-mentioned intelligent fabric.

According to the embodiments of the present disclosure, it is able to detect the ambient temperature by the temperature sensor and switch the intelligent fabric between a warm-keeping state and a ventilation state in accordance with the ambient temperature, thereby to adapt to different scenarios.

DETAILED DESCRIPTION OF THE EMBODIMENTS

The present disclosure will be described hereinafter in conjunction with the drawings and embodiments. The following embodiments are for illustrative purposes only, but shall not be used to limit the scope of the present disclosure.

Figure 1:
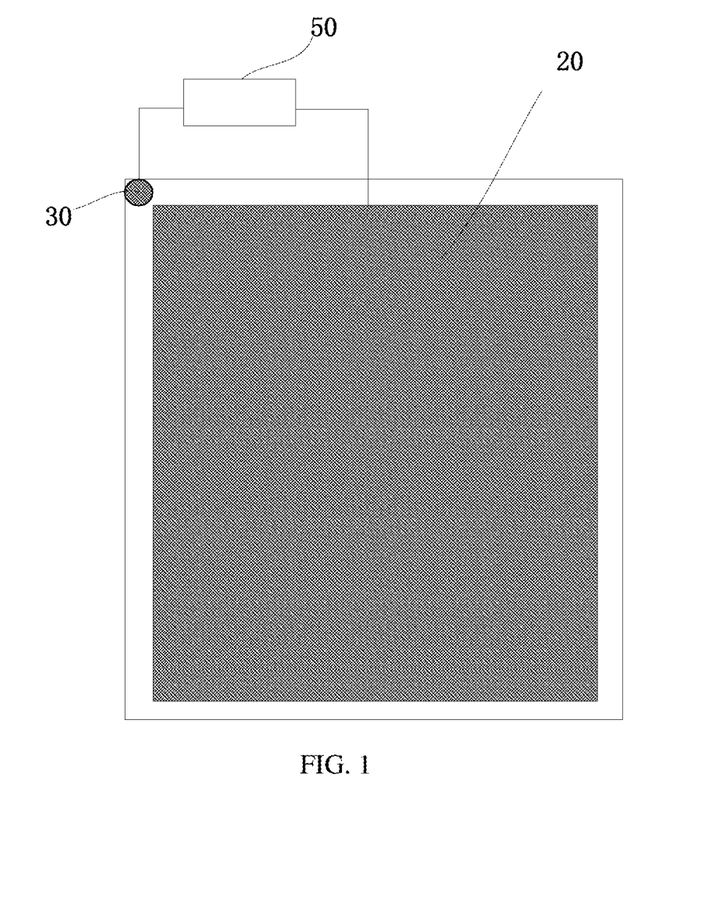
FIG. 1 is a schematic view showing an intelligent fabric in a warm-keeping state according to the first embodiment of the present disclosure.
Figure 2:
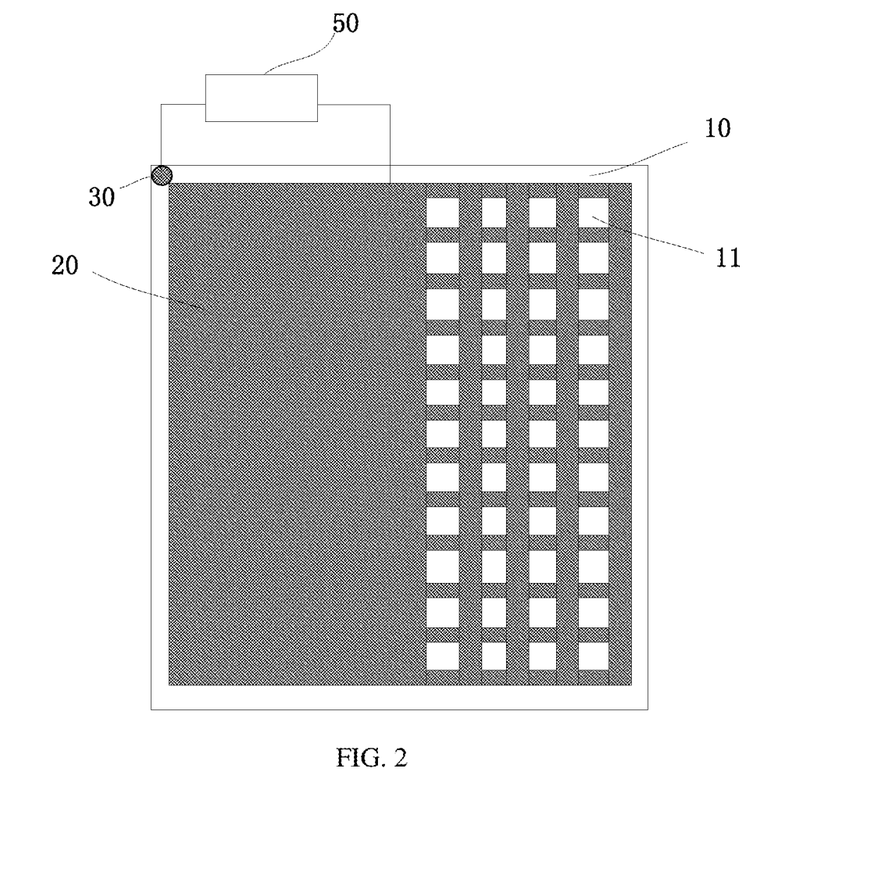
FIGS. 2 and 3 are schematic views showing the intelligent fabric of FIG. 1 in a ventilation state.
Figure 3:
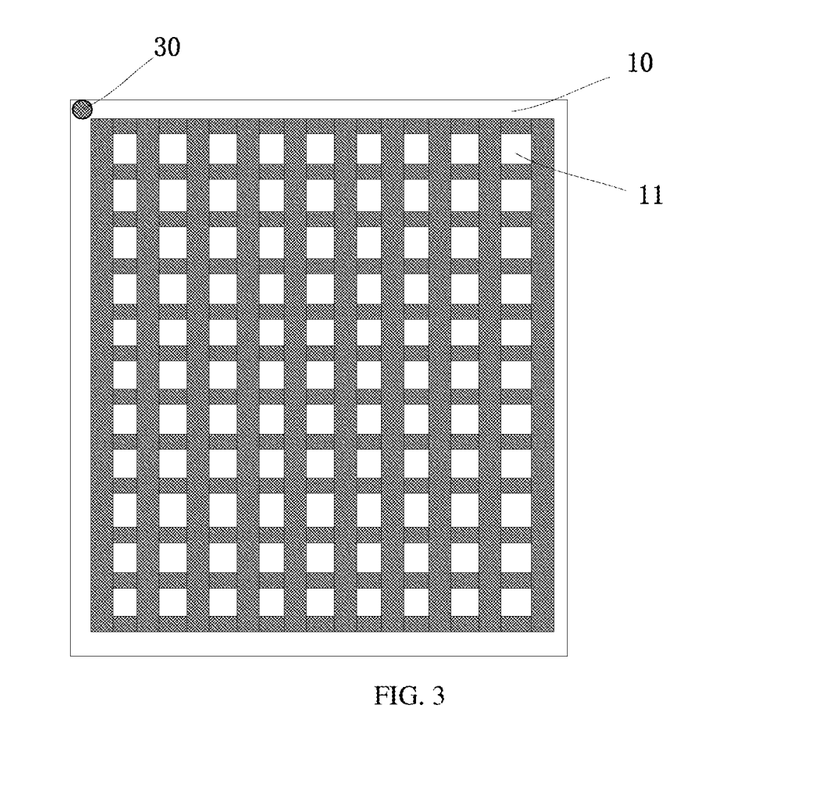

In order to keep a user warm at a low body temperature and dissipate heat rapidly at a high body temperature, the present disclosure provides in some embodiments an intelligent fabric which, as shown in FIGS. 1-3, includes: a base layer 10 provided with vent holes 11 and a thermal insulation layer 20 arranged on the base layer 10 and capable of being moved relative to the base layer 10; a temperature sensor 30 configured to detect temperature information; and a controller 50 connected to the temperature sensor 30 and the thermal insulation layer 20, and configured to control the thermal insulation layer 20 to be moved relative to the base layer 10 in accordance with the temperature information detected by the temperature sensor 30, so as to switch the thermal insulation layer 20 between a state where the thermal insulation layer 20 covers the vent holes completely (as shown in FIG. 1) and a state where the thermal insulation layer 20 does not cover the vent holes (as shown in FIG. 3), or among the state where the thermal insulation layer 20 covers the vent holes completely, a state where the thermal insulation layer 20 covers a portion of the vent holes (as shown in FIG. 2), and the state where the thermal insulation layer 20 does not cover the vent holes.

Figure 4:
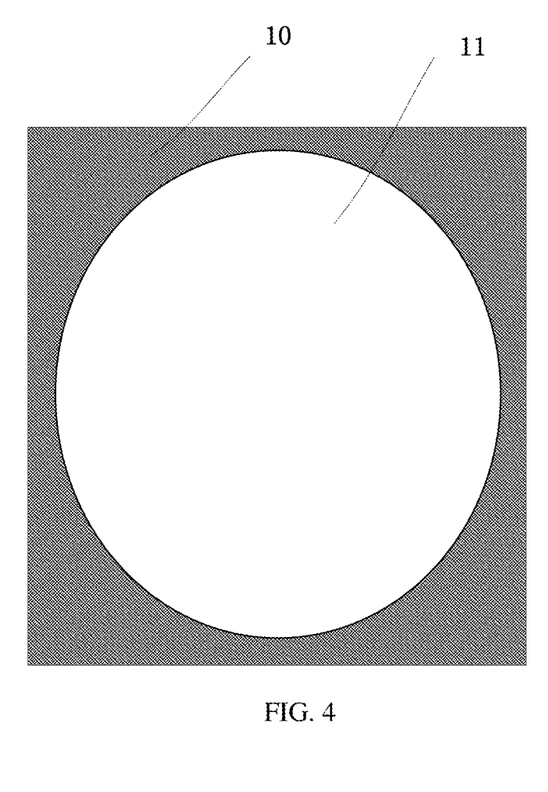
FIG. 4 is a schematic view showing the intelligent fabric according to the second embodiment of the present disclosure.

The number of the vent holes 11 in the base layer 10 is not particularly defined herein. For example, there may be one (as shown in FIG. 4), two or more vent holes 11. In addition, a shape of the vent hole 11 is not particularly defined herein either. For example, the vent hole 11 may be of a circular or rectangular shape. It should be appreciated that, the larger the size of the vent hole 11, the better the resultant ventilation effect. In the case that the vent hole 11 is of a large size, optionally, a mesh with an excellent ventilation effect may also be arranged on the vent hole 11, so as to block foreign matters such as sand.

The thermal insulation layer 20 needs to be made of a fabric having a warm-keeping function. In some embodiments of the present disclosure, the thermal insulation layer 20 may be switched between two states, i.e., the state where it completely covers the vent holes 11 and the state where it does not cover the vent holes 11 at all. In some other embodiments of the present disclosure, the thermal insulation layer 20 may be switched among three states, i.e., the state where it completely covers the vent holes 11, the state where it does not cover the vent holes 11, and the state where it covers a portion of the vent holes 11. In the case that the thermal insulation layer 20 covers a portion of the vent holes 11, there may be only one state, in which, e.g. a half of the total number of the vent holes 11 may be covered; of course, there may be more than one state, in which, e.g. one third of, a half of or two thirds of the total number of the vent holes 11 may be covered. In the case that the thermal insulation layer 20 covers the vent holes 11 completely, the intelligent fabric is in a warm-keeping state, and in the case that the thermal insulation layer 20 covers a portion of the vent holes 11, or does not cover the vent holes 11, the intelligent fabric is in a ventilation state.

One or more temperature sensors 30 may be arranged on the base layer 10. To be specific, in the case that an ambient temperature detected by the temperature sensor 30 is relatively high, it means that it is required to dissipate the heat. At this time, the controller may control the thermal insulation layer 20 to move in such a manner as to expose the vent holes 11, thereby to dissipate the heat. In the case that the ambient temperature detected by the temperature sensor 30 is relatively low, it means that it is required to keep warm. At this time, the controller may control the thermal insulation layer 20 to move in such a manner as to cover the vent holes 11, thereby to prevent the heat from dissipating.

According to the embodiments of the present disclosure, it is able to detect the ambient temperature by the temperature sensor and switch the intelligent fabric between a warm-keeping state and a ventilation state in accordance with the ambient temperature, thereby to adapt to different scenarios.

Figure 11:
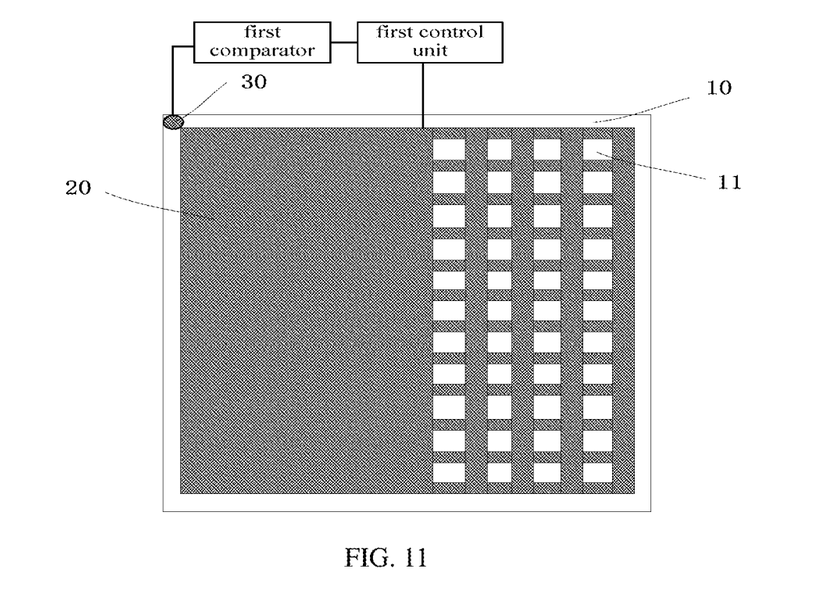
FIG. 11 is a schematic view showing the intelligent fabric according to the fifth embodiment of the present disclosure.

Referring to FIG. 11, in the embodiment where the thermal insulation layer 20 has two states, i.e., the state where the thermal insulation layer 20 completely covers the vent holes 11 and the state where the thermal insulation layer 20 does not cover the vent holes 11, the controller may includes: a first comparator connected to the temperature sensor 30 and configured to compare the temperature information detected by the temperature sensor 30 with a temperature threshold (which may be set in accordance with the practical need, e.g., 36.5° C.); and a first control unit connected to the first comparator and the thermal insulation layer 20, and configured to, in the case that the first comparator determines that the temperature information detected by the temperature sensor 30 is less than or equal to the temperature threshold, control the thermal insulation layer 20 to completely cover the vent holes 11, and in the case that the first comparator determines that the temperature information detected by the temperature sensor 30 is greater than the temperature threshold, enable the thermal insulation layer 20 not to cover the vent holes 11.

In this embodiment of the present disclosure, the thermal insulation layer may merely be switched between two states, so as to simplify a control mode and reduce the production cost.

Figure 12:
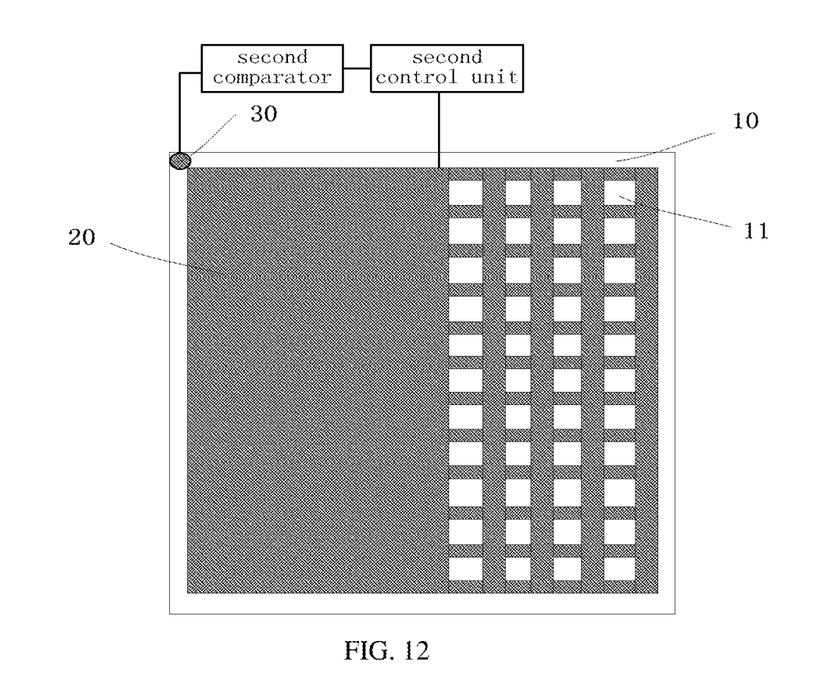
FIG. 12 is a schematic view showing the intelligent fabric according to the sixth embodiment of the present disclosure.

Referring to FIG. 12, in the embodiment where the thermal insulation layer 20 has three states, i.e., the state where the thermal insulation layer 20 completely covers the vent holes 11, the state where the thermal insulation layer 20 covers a portion of the vent holes 11, and the state where the thermal insulation layer 20 does not cover the vent holes 11, the controller may includes: a second comparator connected to the temperature sensor 30, and configured to compare the temperature detected by the temperature sensor 30 with a first threshold and a second threshold greater than the first threshold; and a second control unit connected to the second comparator and the thermal insulation layer 20, and configured to, in the case that the second comparator determines that the temperature information detected by the temperature sensor 30 is less than or equal to the first threshold, control the thermal insulation layer 20 to completely cover the vent holes 11, in the case that the second comparator determines that the temperature information detected by the temperature sensor 30 is between the first threshold and the second threshold, control the thermal insulation layer 20 to cover a portion of the vent holes 11, and in the case that the second comparator determines that the temperature information detected by the temperature sensor 30 is greater than or equal to the second threshold, control the thermal insulation layer 20 not to cover the vent holes 11. The first threshold and the second threshold are provided so as to define a temperature range. The values of the first and second thresholds may be set in accordance with the practical need, e.g., the first threshold may be 36° C., and the second threshold may be 37° C.

In this embodiment of the present disclosure, the thermal insulation layer 20 may be switched among three states, so as to meet the requirements in a better manner.

In the embodiments of the present disclosure, in the case that there are more than one temperature sensors 30, the states of the thermal insulation layer 20 may be switched as long as the temperature detected by any one of the temperature sensors meets the condition.

The structures of the base layer 10, the thermal insulation layer 20 and the controller will be described hereinafter by an example.

Figure 5:
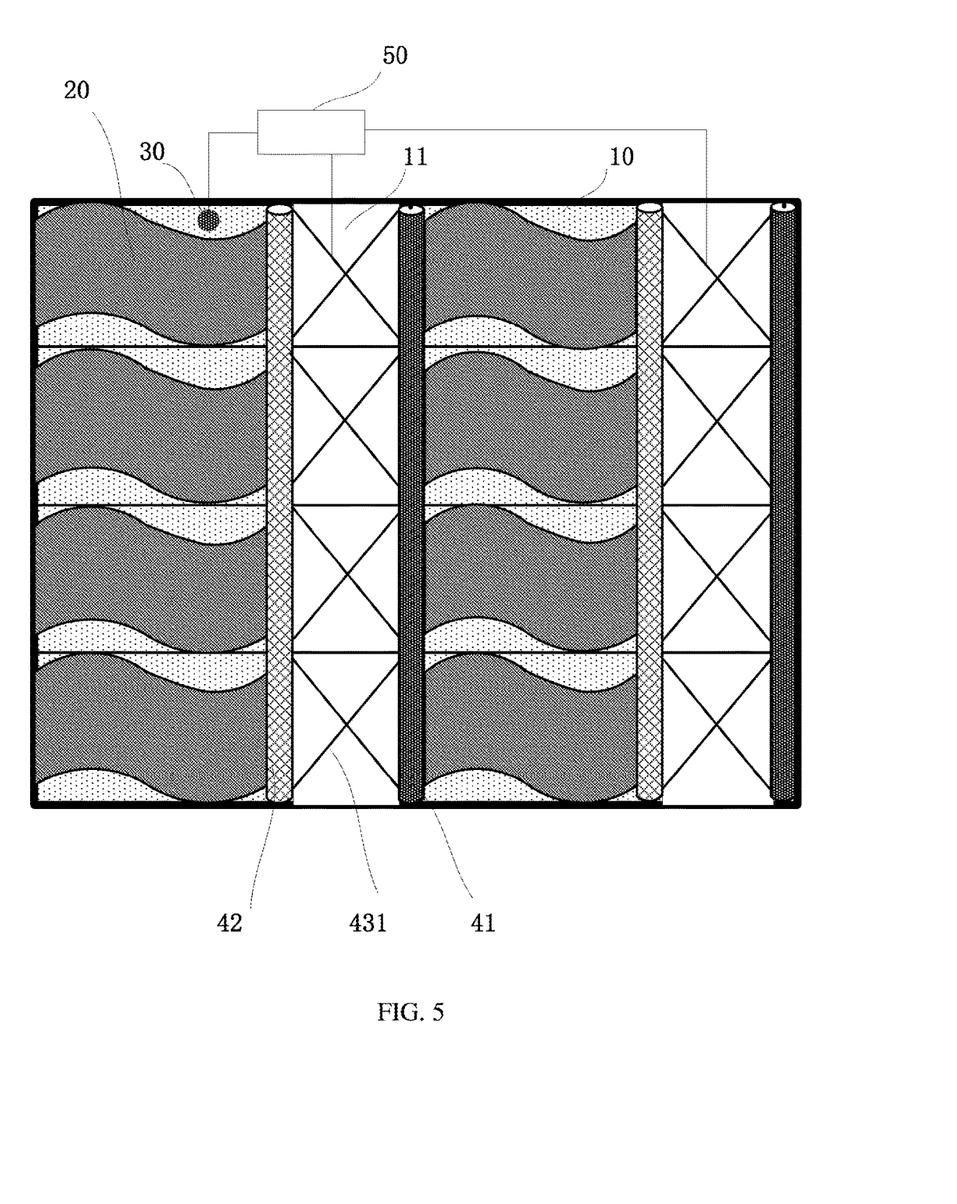
FIG. 5 is a schematic view showing the intelligent fabric in the ventilation state according to the third embodiment of the present disclosure.
Figure 6:
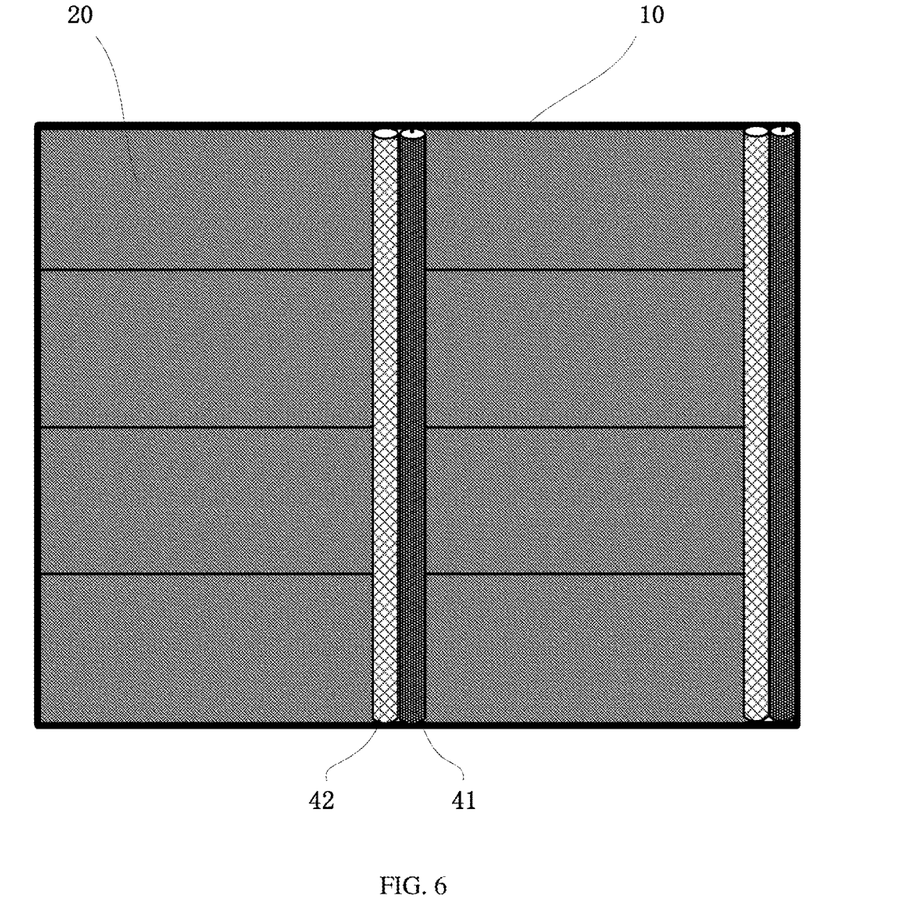
FIG. 6 is a schematic view showing the intelligent fabric of FIG. 5 in a thermal-insulation state.

Referring to FIGS. 5 and 6, which are schematic views showing the intelligent fabric according to the third embodiment of the present disclosure, the intelligent fabric includes: the base layer 10 provided with the vent holes 11 and the thermal insulation layer 20 arranged on the base layer 10 and capable of being moved relative to the base layer 10; the temperature sensor 30 arranged on the base layer 10 and configured to detect the temperature information; and the controller 50 connected to the temperature sensor 30 and the thermal insulation layer 20, and configured to control the thermal insulation layer 20 to be moved relative to the base layer 10 in accordance with the temperature information detected by the temperature sensor 30, so as to switch the thermal insulation layer 20 between the state where the thermal insulation layer 20 covers the vent holes completely and the state where the thermal insulation layer 20 does not cover the vent holes, or among the state where the thermal insulation layer 20 covers the vent holes completely, the state where the thermal insulation layer 20 covers a portion of the vent holes, and the state where the thermal insulation layer 20 does not cover the vent holes.

The controller includes: a stationary rod 41 fixed to a first end of the vent hole 11; a mobile rod 42 movably arranged on the vent hole 11 and opposite to the stationary rod 41, and capable of being moved along the vent hole 11 close to, or away from, the stationary rod 41; and a driving member connected to the mobile rod 42, and configured to drive the mobile rod 42 to be moved close to, or away from, the stationary rod 41 in accordance with the temperature information detected by the temperature sensor 30.

In this embodiment, one end of the thermal insulation layer 20 is connected to the mobile rod 42, and the other end of the thermal insulation layer 20 is fixed onto a second end of the vent hole 11 which is opposite to the first end of the vent hole 11. In the case that the mobile rod 42 is moved close to the stationary rod 41, more vent holes 11 are covered by the thermal insulation layer 20, and in the case that the mobile rod 42 is moved away from the stationary rod 41, fewer vent holes 11 are covered by the thermal insulation layer 20.

The thermal insulation layer 20 may be made of a flexible, foldable fabric or an elastic, telescopic fabric.

In the case that the thermal insulation layer 20 is made of the flexible, foldable fabric and the mobile rod 42 is moved away from the stationary rod 41, the thermal insulation layer 20 may be folded or wound onto the mobile rod 42. In the case that the mobile rod 42 is moved close to the stationary rod 41, the thermal insulation layer 20 may be extended.

In the case that the thermal insulation layer 20 is made of the elastic, telescopic fabric and the mobile rod 42 is moved away from the stationary rod 41, the thermal insulation layer 20 may be in a retraction state. In the case that the mobile rod 42 is moved close to the stationary rod 41, the thermal insulation layer 20 may be in an extension state.

In another embodiment of the present disclosure, one end of the thermal insulation layer 20 may be connected to the mobile rod 42, and the other end of the thermal insulation layer 20 may be fixed onto the stationary rod 41. In the case that the mobile rod 42 is moved close to the stationary rod 41, fewer vent holes 11 are covered by the thermal insulation layer 20, and in the case that the mobile rod 42 is moved away from the stationary rod 41, more vent holes 11 are covered by the thermal insulation layer 20.

Identically, the thermal insulation layer 20 may be made of a flexible, foldable fabric or an elastic, telescopic fabric.

In the case that the thermal insulation layer 20 is made of the flexible, foldable fabric and the mobile rod 42 is moved close to the stationary rod 41, the thermal insulation layer 20 may be folded or wound onto the mobile rod 42. In the case that the mobile rod 42 is moved away from the stationary rod 41, the thermal insulation layer 20 may be extended.

In the case that the thermal insulation layer 20 is made of the elastic, telescopic fabric and the mobile rod 42 is moved close to the stationary rod 41, the thermal insulation layer 20 may be in a retraction state. In the case that the mobile rod 42 is moved away from the stationary rod 41, the thermal insulation layer 20 may be in an extension state.

In the above embodiment of the present disclosure, the driving member may include: an elastic, telescopic member 431 configured to connect the stationary rod 41 to the mobile rod 42; a control member 50 connected to the elastic, telescopic member 431, and configured to control a telescopic movement of the elastic, telescopic member 431 in accordance with the temperature information detected by the temperature sensor 30, so as to drive the mobile rod 42 to be moved close to, or away from, the stationary rod 41.

Figure 13:
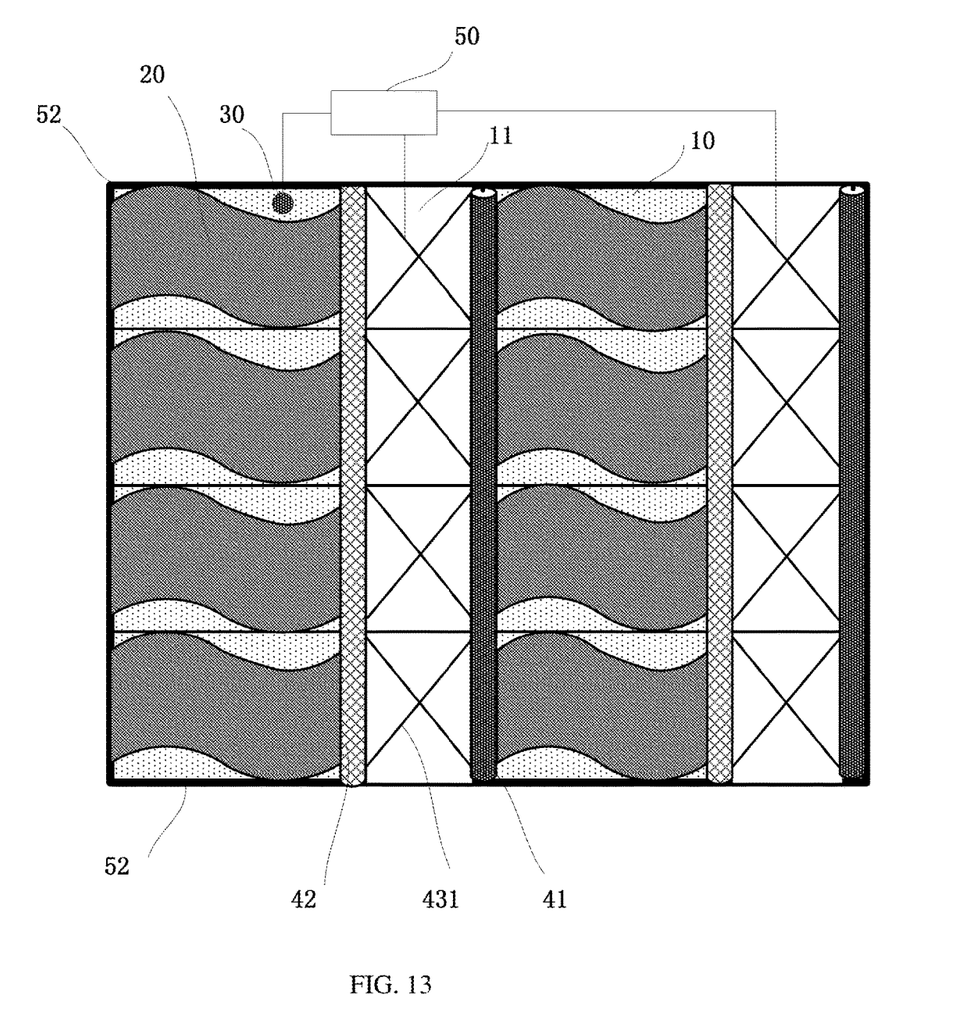
FIG. 13 is a schematic view showing the intelligent fabric in the ventilation state according to the seventh embodiment of the present disclosure.

Of course, in some other embodiments of the present disclosure, the driving member may of any other structures. For example, the driving member may include two sliding rails 52 arranged opposite to each other and a control member (as shown in FIG. 13). At this time, the two ends of the mobile rod 42 are arranged in the two sliding rails 52 respectively, and the control member is configured to control the movement of the mobile rod 42 along the sliding rails 52 in accordance with the temperature information detected by the temperature sensor 30, so as to be moved close to, or away from, the stationary rod 41.

Figure 7:
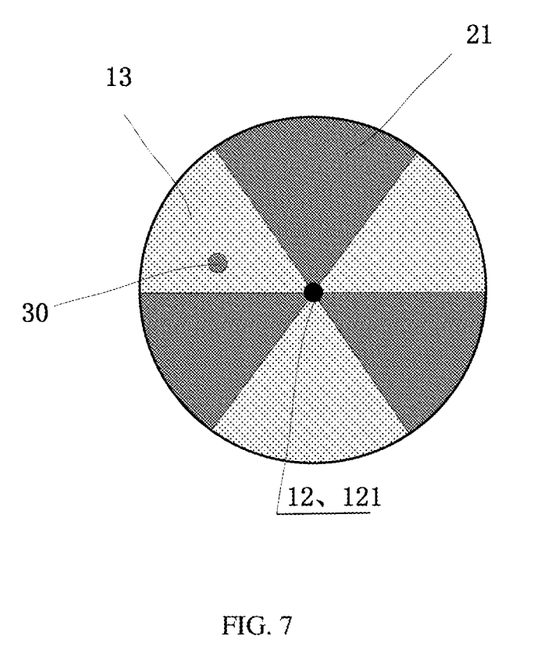
FIG. 7 is a schematic view showing the intelligent fabric in the warm-keeping state according to the fourth embodiment of the present disclosure.
Figure 8:
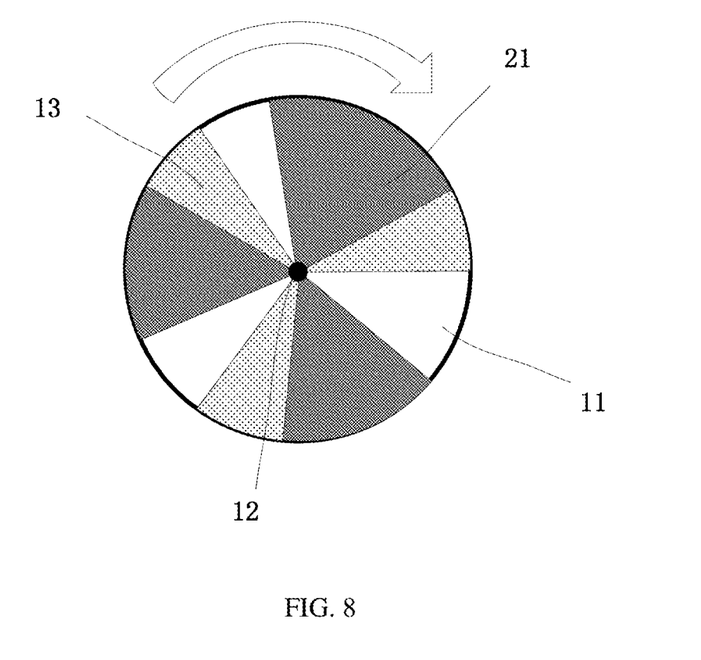
FIGS. 8 and 9 are schematic views showing the intelligent fabric of FIG. 7 in the ventilation state.
Figure 9:
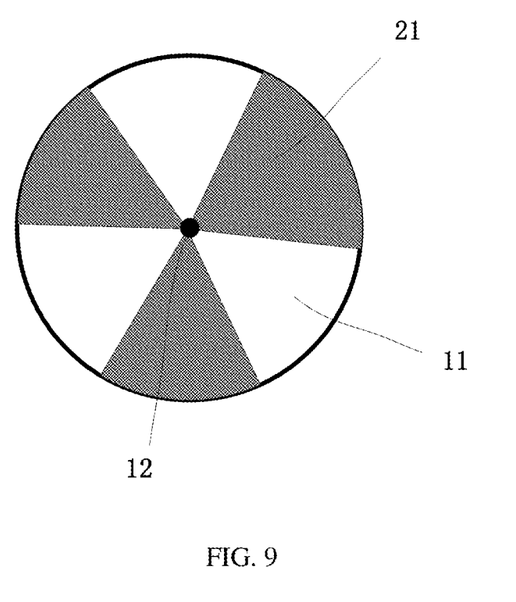

Referring to FIGS. 7-9, which are schematic views showing the intelligent fabric according to the fourth embodiment of the present disclosure, the intelligent fabric includes: the base layer provided with the vent holes 11 and the thermal insulation layer arranged on the base layer and capable of being moved relative to the base layer; the temperature sensor 30 arranged on the base layer and configured to detect the temperature information; and the controller connected to the temperature sensor 30 and the thermal insulation layer, and configured to control the thermal insulation layer to be moved relative to the base layer in accordance with the temperature information detected by the temperature sensor 30, so as to switch the thermal insulation layer between the state where the thermal insulation layer covers the vent holes 11 completely and the state where the thermal insulation layer does not cover the vent holes 11, or among the state where the thermal insulation layer covers the vent holes completely, the state where the thermal insulation layer covers a portion of the vent holes, and the state where the thermal insulation layer does not cover the vent holes. The base layer includes: a stationary spindle 12, and a plurality of stationary sectors 13 arranged fixedly around the stationary spindle 12. The stationary sectors 13 are arranged at intervals, and the vent hole 11 is arranged between the adjacent stationary sectors 13. The thermal insulation layer includes a plurality of rotatable sectors 21 arranged around the stationary spindle 12. The rotatable sectors 21 are arranged at intervals, and each of the rotatable sectors 21 has a shape adapted to a shape of the vent hole 11. Optionally, a shape and a size of each rotatable sector 21 may be identical to those of each stationary sector 13.

The controller includes a driving member, e.g., an electric motor 121 arranged on the stationary spindle 12, and an output shaft of the electric motor 121 is connected to the rotatable sectors 21. The driving member is configured to drive the rotatable sectors 21 to rotate around the stationary spindle 12 in accordance with the temperature information detected by the temperature sensor 30, so as to enable the rotatable sectors 21 to cover the vent holes 11 partially, cover the vent holes 11 completely, or not to cover the vent holes 11.

The stationary sector 13 and the rotatable sector 21 may be made of a common fabric or a warm-keeping fabric.

The present disclosure further provides in some embodiments an intelligent shoe. The intelligent shoe includes a sole and an upper portion arranged on the sole, wherein the upper portion is at least partially made of the above-mentioned intelligent fabric.

Figure 10:
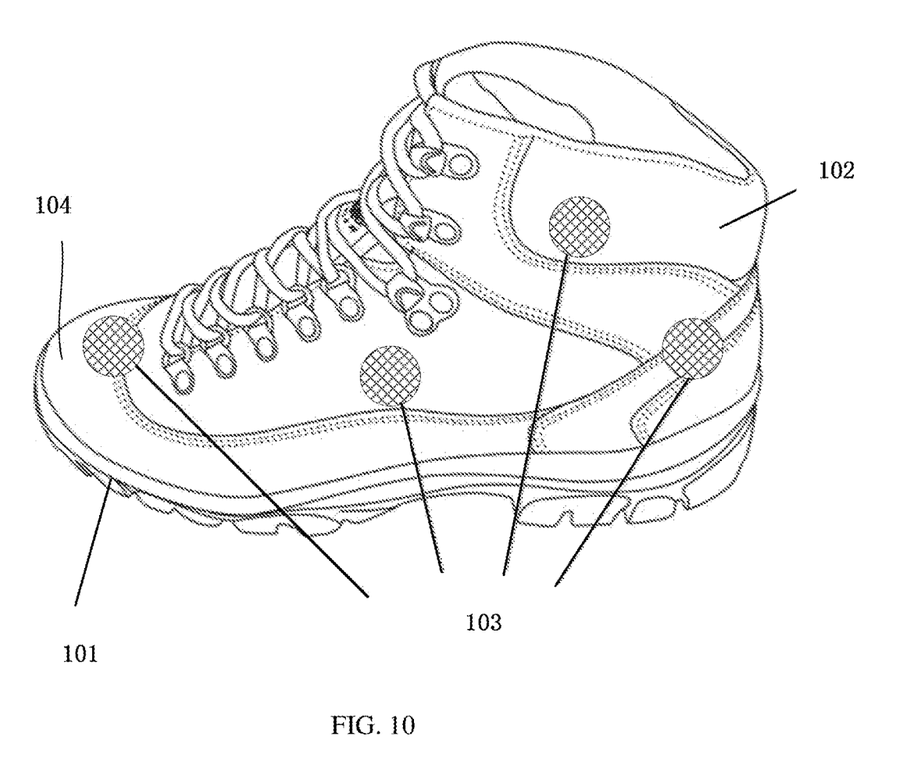
FIG. 10 is a schematic view showing an intelligent shoe according to one embodiment of the present disclosure.

Referring to FIG. 10, which is a schematic view showing the intelligent shoe according to one embodiment of the present disclosure, the intelligent shoe includes the sole 101 and a shoe body 102. The intelligent fabric 103 may be arranged at positions corresponding to an upper surface, a side surface and an ankle portion of the shoe body 102 where sweat easily occurs. The other portions of the shoe body 102 may be made of a common fabric 104. In other words, the intelligent shoe may be made by joining the common fabric 104 and the intelligent fabric 103.

In the case that the user is dressed in the above-mentioned intelligent shoe, it is unnecessary to take the ambient temperature into consideration during the exercise, i.e., it is able to keep warm and rapidly dissipate the heat generated during the exercise, thereby to prevent the user from being adversely affected due to a difference in the temperatures during the exercise and before or after the exercise.

For example, in winter, the ambient temperature is relatively low, and a body temperature of the user's feet is low before and after the exercise. At this time, the temperature sensor may detect the body temperature, so as to enable the intelligent fabric to be in the warm-keeping state. In the case that the user starts to take exercises and the body temperature of the user's feet increases gradually with sweat occurring at some portions of the user's feet, the temperature sensor may detect the increasing body temperature, so as to switch the intelligent fabric to the ventilation state, thereby to dissipate the heat in time and meanwhile maintain the temperature at the portions of the user's feet where sweat seldom occurs. In the case that the user has completed the exercises, the body temperature may decrease rapidly if the intelligent shoe continues to be in the ventilation state, and thus the user may easily catch a cold. At this time, the intelligent fabric may be switched from the ventilation state to the warm-keeping state, so as to maintain the body temperature and keeps the user healthy.

The present disclosure further provides in some embodiments an intelligent garment at least partially made of the above-mentioned intelligent fabric.

The above are merely the preferred embodiments of the present disclosure. Obviously, a person skilled in the art may make further modifications and improvements without departing from the spirit of the present disclosure, and these modifications and improvements shall also fall within the scope of the present disclosure.

What is claimed is:

1. An intelligent fabric, comprising:
   a base layer provided with vent holes;
   a thermal insulation layer arranged on the base layer and movable relative to the base layer;
   a temperature sensor configured to detect temperature information; and
   a controller connected to the temperature sensor and the thermal insulation layer, and configured to control the thermal insulation layer to be moved relative to the base layer in accordance with the temperature information detected by the temperature sensor, so as to switch the thermal insulation layer between a state where the thermal insulation layer covers the vent holes completely and a state where the thermal insulation layer does not cover the vent holes, or among the state where the thermal insulation layer covers the vent holes completely, a state where the thermal insulation layer covers a portion of the vent holes, and the state where the thermal insulation layer does not cover the vent holes,
   wherein in the case that the thermal insulation layer is switched between the state where the thermal insulation layer covers the vent holes completely and the state where the thermal insulation layer does not cover the vent holes, the controller comprises:
   a first comparator connected to the temperature sensor and configured to compare the temperature information detected by the temperature sensor with a temperature threshold; and a first control unit connected to the first comparator and the thermal insulation layer, and configured to, in the case that the first comparator determines that the temperature information detected by the temperature sensor is less than or equal to the temperature threshold, control the thermal insulation layer to completely cover the vent holes, and in the case that the first comparator determines that the temperature information detected by the temperature sensor is greater than the temperature threshold, enable the thermal insulation layer not to cover the vent holes.

2. The intelligent fabric according to claim 1, wherein in the case that the thermal insulation layer is switched among the state where the thermal insulation layer covers the vent holes completely, the state where the thermal insulation layer covers a portion of the vent holes and the state where the thermal insulation layer does not cover the vent holes, the controller comprises:
   a second comparator connected to the temperature sensor, and configured to compare the temperature detected by the temperature sensor with a first threshold and a second threshold greater than the first threshold; and
   a second control unit connected to the second comparator and the thermal insulation layer, and configured to, in the case that the second comparator determines that the temperature information detected by the temperature sensor is less than or equal to the first threshold, control the thermal insulation layer to completely cover the vent holes, in the case that the second comparator determines that the temperature information detected by the temperature sensor is between the first threshold and the second threshold, control the thermal insulation layer to cover a portion of the vent holes, and in the case that the second comparator determines that the temperature information detected by the temperature sensor is greater than or equal to the second threshold, control the thermal insulation layer not to cover the vent holes.

3. The intelligent fabric according to claim 1, wherein the controller comprises:
   a stationary rod fixed onto the base layer;
   a mobile rod movably arranged on the base layer and opposite to the stationary rod, and movable along the base layer close to, or away from, the stationary rod; and
   a driving member connected to the mobile rod, and configured to drive the mobile rod to be moved close to, or away from, the stationary rod in accordance with the temperature information detected by the temperature sensor,
   wherein one end of the thermal insulation layer is connected to the mobile rod, and the other end of the thermal insulation layer is fixed onto one end of the base layer, in the case that the mobile rod is moved close to the stationary rod, more vent holes are covered by the thermal insulation layer, and in the case that the mobile rod is moved away from the stationary rod, fewer vent holes are covered by the thermal insulation layer.

4. The intelligent fabric according to claim 3, wherein the driving member comprises:
   an elastic, telescopic member configured to connect the stationary rod to the mobile rod; and
   a control member connected to the elastic, telescopic member, and configured to control a telescopic movement of the elastic, telescopic member in accordance with the temperature information detected by the temperature sensor, so as to drive the mobile rod to be moved close to, or away from, the stationary rod.

5. The intelligent fabric according to claim 4, wherein the driving member further comprises two opposite sliding rails, and two ends of the mobile rod are arranged in the two sliding rails respectively.

6. The intelligent fabric according to claim 1, wherein the controller comprises:
   a stationary rod fixed onto the base layer;
   a mobile rod movably arranged on the base layer and opposite to the stationary rod, and movable along the base layer close to, or away from, the stationary rod; and
   a driving member connected to the mobile rod, and configured to drive the mobile rod to be moved close to, or away from, the stationary rod in accordance with the temperature information detected by the temperature sensor,
   wherein one end of the thermal insulation layer is connected to the mobile rod, and the other end of the thermal insulation layer is fixed onto the stationary rod, in the case that the mobile rod is moved close to the stationary rod, fewer vent holes are covered by the thermal insulation layer, and in the case that the mobile rod is moved away from the stationary rod, more vent holes are covered by the thermal insulation layer.

7. The intelligent fabric according to claim 6, wherein the driving member comprises:
   an elastic, telescopic member configured to connect the stationary rod to the mobile rod; and
   a control member connected to the elastic, telescopic member, and configured to control a telescopic movement of the elastic, telescopic member in accordance with the temperature information detected by the temperature sensor, so as to drive the mobile rod to be moved close to, or away from, the stationary rod.

8. The intelligent fabric according to claim 1, wherein the base layer includes a first end and a second end opposite to the first end;
   the controller comprises: a mobile rod movably arranged on the base layer and movable along the base layer to close to, or away from, the second end of the base layer; and a driving member connected to the mobile rod and configured to drive the mobile rod to be moved close to, or away from, the second end of the base layer in accordance with the temperature information detected by the temperature sensor; and
   one end of the thermal insulation layer is fixed to the first end of the base layer, and the other end of the thermal insulation layer is connected to the mobile rod, in the case that the mobile rod is moved close to the second end of the base layer, more vent holes are covered by the thermal insulation layer, and in the case that the mobile rod is moved away from the second end of the base layer, fewer vent holes are covered by the thermal insulation layer.

9. The intelligent fabric according to claim 8, wherein the driving member comprises:
   an elastic, telescopic member configured to connect the mobile rod to the second end of the base layer; and
   a control member connected to the elastic, telescopic member, and configured to control a telescopic movement of the elastic, telescopic member in accordance with the temperature information detected by the temperature sensor, so as to drive the mobile rod to be moved close to, or away from, the second end of the base layer.

10. The intelligent fabric according to claim 1, wherein the thermal insulation layer is made of a flexible, foldable fabric or an elastic, telescopic fabric.

11. The intelligent fabric according to claim 1, wherein
   the base layer comprises a stationary spindle, and a plurality of stationary sectors arranged fixedly around the stationary spindle;
   the stationary sectors are arranged at intervals, and the vent hole is arranged between the adjacent stationary sectors;
   the thermal insulation layer comprises a plurality of rotatable sectors arranged around the stationary spindle;
   the rotatable sectors are arranged at intervals, and each of the rotatable sectors has a shape adapted to a shape of the vent hole; and
   the controller comprises a driving member connected to the rotatable sectors and configured to drive the rotatable sectors to rotate around the stationary spindle in accordance with the temperature information detected by the temperature sensor, so as to enable the rotatable sectors to cover the vent holes partially, cover the vent holes completely, or not to cover the vent holes.

12. An intelligent shoe, comprising a sole and an upper portion arranged on the sole, wherein at least a part of the upper portion is made of the intelligent fabric according to claim 1.

13. The intelligent shoe according to claim 12, wherein the intelligent shoe is made by joining a common fabric and the intelligent fabric.

14. The intelligent shoe according to claim 13, wherein the intelligent fabric is arranged at a position corresponding to an upper surface, a side surface or an ankle portion of the upper portion.

15. The intelligent shoe according to claim 12, wherein in the case that the thermal insulation layer is switched among the state where the thermal insulation layer covers the vent holes completely, the state where the thermal insulation layer covers a portion of the vent holes and the state where the thermal insulation layer does not cover the vent holes, the controller comprises:
   a second comparator connected to the temperature sensor, and configured to compare the temperature detected by the temperature sensor with a first threshold and a second threshold greater than the first threshold; and
   a second control unit connected to the second comparator and the thermal insulation layer, and configured to, in the case that the second comparator determines that the temperature information detected by the temperature sensor is less than or equal to the first threshold, control the thermal insulation layer to completely cover the vent holes, in the case that the second comparator determines that the temperature information detected by the temperature sensor is between the first threshold and the second threshold, control the thermal insulation layer to cover a portion of the vent holes, and in the case that the second comparator determines that the temperature information detected by the temperature sensor is greater than or equal to the second threshold, control the thermal insulation layer not to cover the vent holes.

16. An intelligent garment at least partially made of the intelligent fabric according to claim 1.

17. The intelligent garment according to claim 16, wherein in the case that the thermal insulation layer is switched between the state where the thermal insulation layer covers the vent holes completely and the state where the thermal insulation layer does not cover the vent holes, the controller comprises:
  a first comparator connected to the temperature sensor and configured to compare the temperature information detected by the temperature sensor with a temperature threshold; and
  a first control unit connected to the first comparator and the thermal insulation layer, and configured to, in the case that the first comparator determines that the temperature information detected by the temperature sensor is less than or equal to the temperature threshold, control the thermal insulation layer to completely cover the vent holes, and in the case that the first comparator determines that the temperature information detected by the temperature sensor is greater than the temperature threshold, enable the thermal insulation layer not to cover the vent holes.

18. The intelligent garment according to claim 16, wherein in the case that the thermal insulation layer is switched among the state where the thermal insulation layer covers the vent holes completely, the state where the thermal insulation layer covers a portion of the vent holes and the state where the thermal insulation layer does not cover the vent holes, the controller comprises:
  a second comparator connected to the temperature sensor, and configured to compare the temperature detected by the temperature sensor with a first threshold and a second threshold greater than the first threshold; and
  a second control unit connected to the second comparator and the thermal insulation layer, and configured to, in the case that the second comparator determines that the temperature information detected by the temperature sensor is less than or equal to the first threshold, control the thermal insulation layer to completely cover the vent holes, in the case that the second comparator determines that the temperature information detected by the temperature sensor is between the first threshold and the second threshold, control the thermal insulation layer to cover a portion of the vent holes, and in the case that the second comparator determines that the temperature information detected by the temperature sensor is greater than or equal to the second threshold, control the thermal insulation layer not to cover the vent holes.

19. An intelligent fabric, comprising:
  a base layer provided with vent holes;
  a thermal insulation layer arranged on the base layer movable relative to the base layer;
  a temperature sensor configured to detect temperature information; and
  a controller connected to the temperature sensor and the thermal insulation layer, and configured to control the thermal insulation layer to be moved relative to the base layer in accordance with the temperature information detected by the temperature sensor, so as to switch the thermal insulation layer between a state where the thermal insulation layer covers the vent holes completely and a state where the thermal insulation layer does not cover the vent holes, or among the state where the thermal insulation layer covers the vent holes completely, a state where the thermal insulation layer covers a portion of the vent holes, and the state where the thermal insulation layer does not cover the vent holes,
  wherein the controller comprises:
    a stationary rod fixed onto the base layer;
    a mobile rod movably arranged on the base layer and opposite to the stationary rod, and movable along the base layer close to, or away from, the stationary rod; and
    a driving member connected to the mobile rod, and configured to drive the mobile rod to be moved close to, or away from, the stationary rod in accordance with the temperature information detected by the temperature sensor,
  wherein one end of the thermal insulation layer is connected to the mobile rod, and the other end of the thermal insulation layer is fixed onto one end of the base layer, in the case that the mobile rod is moved close to the stationary rod, more vent holes are covered by the thermal insulation layer, and in the case that the mobile rod is moved away from the stationary rod, fewer vent holes are covered by the thermal insulation layer; or one end of the thermal insulation layer is connected to the mobile rod, and the other end of the thermal insulation layer is fixed onto the stationary rod, in the case that the mobile rod is moved close to the stationary rod, fewer vent holes are covered by the thermal insulation layer, and in the case that the mobile rod is moved away from the stationary rod, more vent holes are covered by the thermal insulation layer.

20. An intelligent fabric, comprising:
  a base layer provided with vent holes;
  a thermal insulation layer arranged on the base layer and movable relative to the base layer;
  a temperature sensor configured to detect temperature information; and
  a controller connected to the temperature sensor and the thermal insulation layer, and configured to control the thermal insulation layer to be moved relative to the base layer in accordance with the temperature information detected by the temperature sensor, so as to switch the thermal insulation layer between a state where the thermal insulation layer covers the vent holes completely and a state where the thermal insulation layer does not cover the vent holes, or among the state where the thermal insulation layer covers the vent holes completely, a state where the thermal insulation layer covers a portion of the vent holes, and the state where the thermal insulation layer does not cover the vent holes,
  wherein the base layer includes a first end and a second end opposite to the first end;
  the controller comprises: a mobile rod movably arranged on the base layer and movable along the base layer to close to, or away from, the second end of the base layer; and a driving member connected to the mobile rod and configured to drive the mobile rod to be moved close to, or away from, the second end of the base layer in accordance with the temperature information detected by the temperature sensor;
  one end of the thermal insulation layer is fixed to the first end of the base layer, and the other end of the thermal insulation layer is connected to the mobile rod, in the case that the mobile rod is moved close to the second end of the base layer, more vent holes are covered by the thermal insulation layer, and in the case that the mobile rod is moved away from the second end of the base layer, fewer vent holes are covered by the thermal insulation layer.

* * * * *